United States Patent
Sumi et al.

(10) Patent No.: US 9,398,899 B2
(45) Date of Patent: Jul. 26, 2016

(54) ULTRASONIC DIAGNOSTIC APPARATUS AND MEDICAL IMAGE PROCESSING APPARATUS

(71) Applicants: Atsushi Sumi, Otawara (JP); Chihiro Shibata, Nasushiobara (JP)

(72) Inventors: Atsushi Sumi, Otawara (JP); Chihiro Shibata, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 694 days.

(21) Appl. No.: 13/671,944

(22) Filed: Nov. 8, 2012

(65) Prior Publication Data
US 2013/0066210 A1  Mar. 14, 2013

Related U.S. Application Data

(63) Continuation of application No. PCT/JP2012/064215, filed on May 31, 2012.

(30) Foreign Application Priority Data

Jun. 6, 2011  (JP) ................. 2011-126733

(51) Int. Cl.
*A61B 8/14*  (2006.01)
*A61B 8/08*  (2006.01)
(Continued)

(52) U.S. Cl.
CPC .............. *A61B 8/5207* (2013.01); *A61B 8/145* (2013.01); *A61B 8/4488* (2013.01); *G01S 7/52038* (2013.01); *G01S 7/52077* (2013.01); *G01S 15/8979* (2013.01)

(58) Field of Classification Search
CPC .... A61B 8/145; A61B 8/4488; A61B 8/5207; G01S 15/8979; G01S 7/52038; G01S 7/52077
See application file for complete search history.

(56) References Cited

U.S. PATENT DOCUMENTS

| 5,873,829 A | 2/1999 | Kamiyama et al. |
| 2005/0101863 A1* | 5/2005 | Kawagishi et al. ........... 600/443 |
| 2009/0264757 A1* | 10/2009 | Yang et al. ................... 600/443 |

FOREIGN PATENT DOCUMENTS

| CN | 1515229 A | 7/2004 |
| CN | 101849840 A | 10/2010 |

(Continued)

OTHER PUBLICATIONS

Written Opinion of the International Searching Authority and International Search Report issued Sep. 4, 2012, in PCT/JP2012/064215.
(Continued)

*Primary Examiner* — Mark Remaly
(74) *Attorney, Agent, or Firm* — Oblon, McClelland, Maier & Neustadt, L.L.P

(57) ABSTRACT

According to one embodiment, a transmission/reception unit generates a reception signal. A signal extraction unit extracts a harmonic signal and fundamental wave signal from the reception signal. A calculation unit calculates a feature amount based on values corresponding to the amplitudes of the harmonic signal and fundamental wave signal. An area determination unit determines an area in a scanned area based on the feature amount and a predetermined threshold. A change unit changes the value corresponding to the amplitude of the harmonic signal in the determined area. An image generation unit generates a corrected harmonic image based on the harmonic signal in the scanned area including the determined area having the changed value.

12 Claims, 9 Drawing Sheets

(51) Int. Cl.
*A61B 8/00* (2006.01)
*G01S 7/52* (2006.01)
*G01S 15/89* (2006.01)

(56) References Cited

FOREIGN PATENT DOCUMENTS

| JP | 2009-018161 | 1/2009 |
|----|-------------|--------|
| JP | 2010-017406 | 1/2010 |
| JP | 2010-514524 | 5/2010 |

OTHER PUBLICATIONS

Takahashi et al., "Native Tissue Harmonic Imaging Method (18-61)", J Med Ultrasonics, vol. 26, No. 12 (1999), pp. 1237-1238.

Ha et al., "Enhanced Detection of Left Atrial Spontaneous Echo Contrast by Transthoracic Harmonic Imaging in Mitral Stenosis", Journal of the American Society of Echocardiography (Sep. 2000), vol. 13, No. 9, pp. 849-854.

Abiru et al., "Nonlinear Propagation of a Pulsed Ultrasound", Shingaku-gihou, vol. 89, No. 155, US89-23 (Jul. 24, 1989), pp. 53-60.

Office Action issued Feb. 10, 2015 in Japanese Patent Application No. 2011-126733.

Combined Chinese Office Action and Search Report issued Apr. 3, 2014, in Chinese Patent Application No. 201280000628.0 with English translation.

International Search Report issued Sep. 4, 2012, in PCT/JP2012/064215.

* cited by examiner

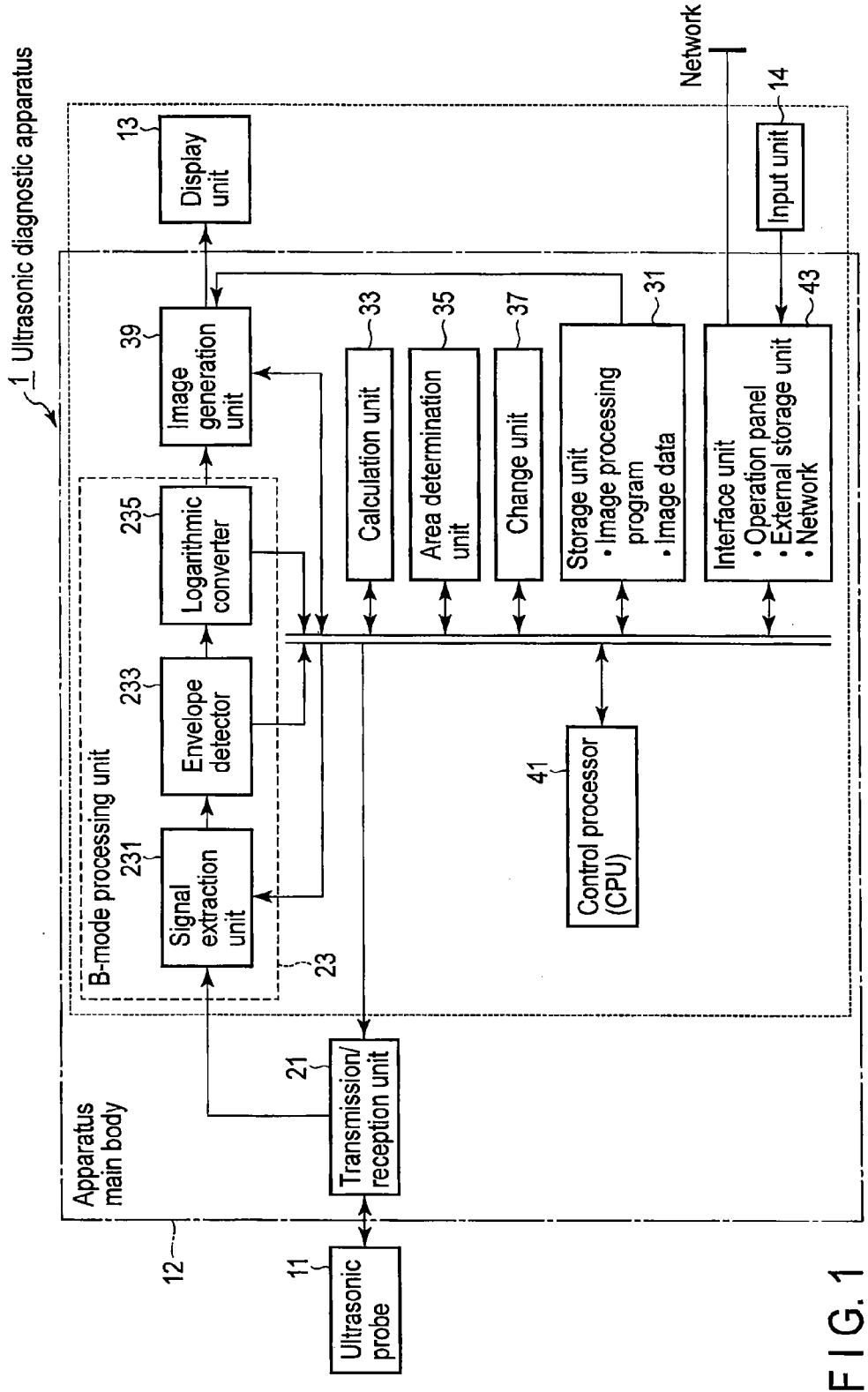
F I G. 1

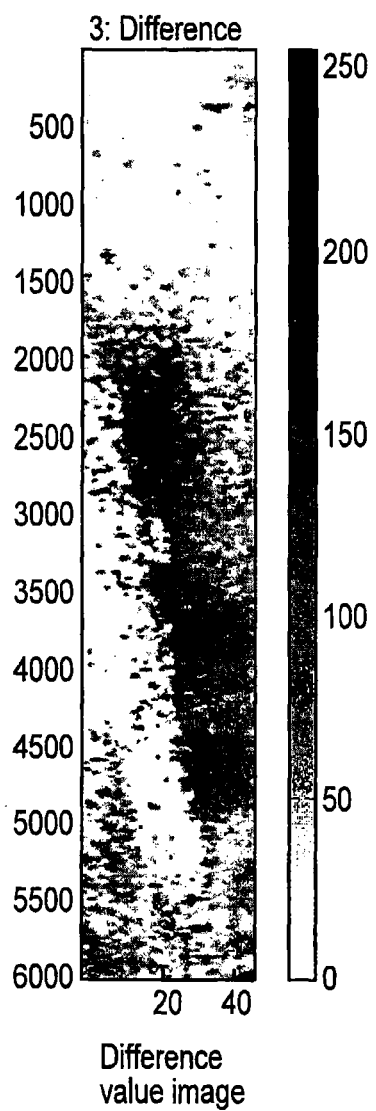
F I G. 5

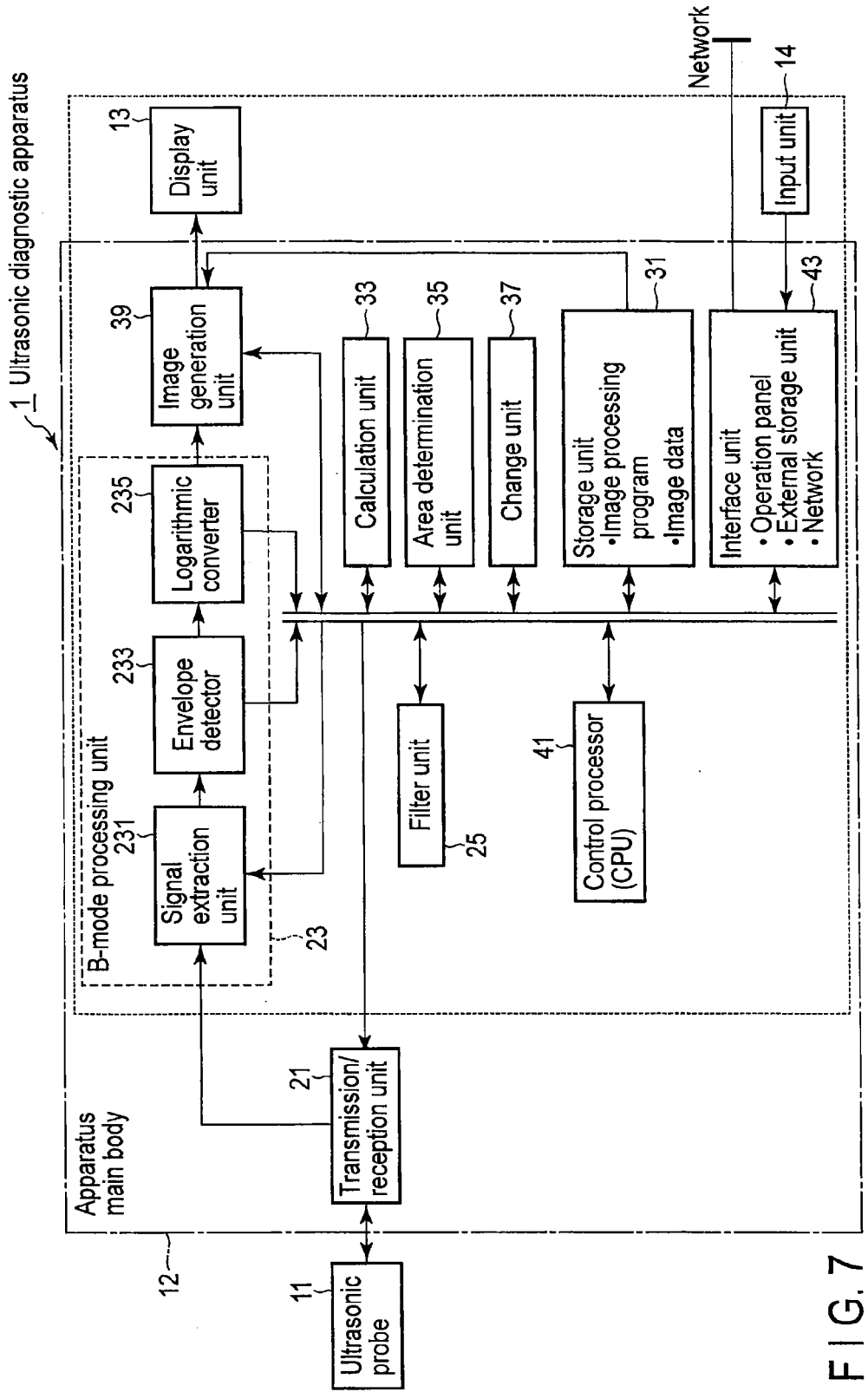
F I G. 7

|  | Amplitude of standardized fundamental wave signal: f | Amplitude of standardized harmonic signal: h | Order of subtraction | |
|---|---|---|---|---|
|  |  |  | h−f | f−h |
| Spontaneous echo | Small | Large | Positive | Negative |
| Structure echo | Large | Small | Negative | Positive |

FIG. 8

ULTRASONIC DIAGNOSTIC APPARATUS AND MEDICAL IMAGE PROCESSING APPARATUS

CROSS REFERENCE TO RELATED APPLICATIONS

This application is a Continuation Application of PCT Application No. PCT/JP2012/064215, filed May 31, 2012 and based upon and claiming the benefit of priority from prior Japanese Patent Application No. 2011-126733, filed Jun. 6, 2011, the entire contents of all of which are incorporated herein by reference.

FIELD

Embodiments described herein relate generally to an ultrasonic diagnostic apparatus and a medical image processing apparatus.

BACKGROUND

Conventionally, there is available a technique (Tissue Harmonic Imaging to be referred to as a THI hereinafter) which images a second-order harmonic component (Tissue Harmonic) contained in an echo signal from a living tissue of an object. A second-order harmonic component is proportional to the square of a sound pressure. For this reason, THI can generate an ultrasonic image with reduced artifacts such as sidelobes.

Scanning a region exhibiting little attenuation of ultrasonic waves may display even weak reflected echoes such as blood flow echoes (to be referred to as spontaneous echoes hereinafter) in the ultrasonic image generated by THI. Displaying such spontaneous echoes makes it difficult for the operator to observe an ultrasonic image. If, for example, spontaneous echoes are reflected echoes from blood and have high intensity, the above region is determined as a living tissue of the object. As a consequence, no color image may be displayed in a region which is ought to be a blood flow region.

BRIEF DESCRIPTION OF THE DRAWINGS

FIG. 1 is a block diagram showing the arrangement of an ultrasonic diagnostic apparatus according to the first embodiment.

FIG. 5 is a view showing an example of a difference value image generated based on difference value frame data according to the first embodiment.

FIG. 7 is a block diagram showing the arrangement of an ultrasonic diagnostic apparatus according to the second embodiment.

FIG. 8 is a view showing an example of a correspondence table between structure and spontaneous echoes and the signs of difference values according to the second embodiment.

DETAILED DESCRIPTION

Figure 2:
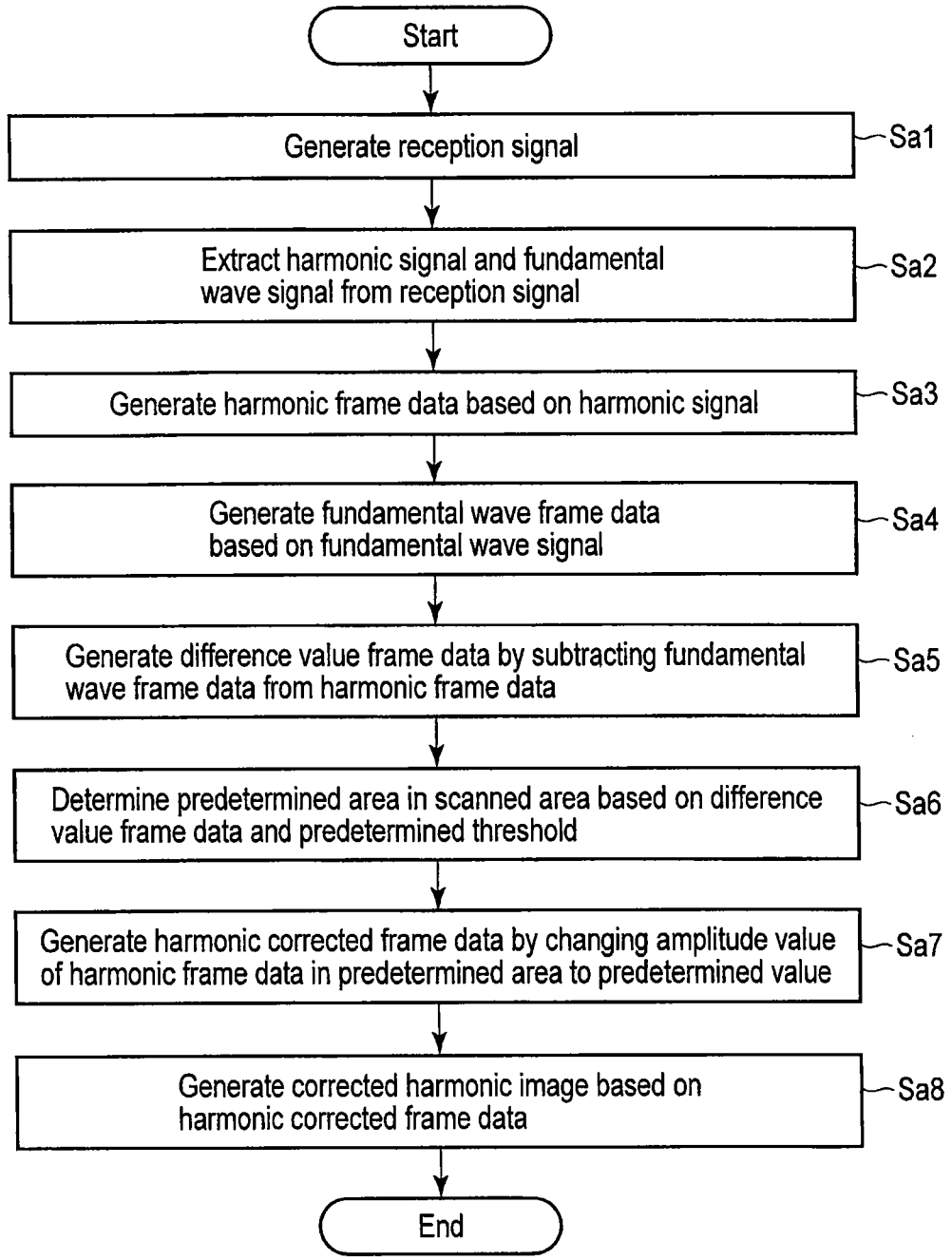
FIG. 2 is a flowchart showing a procedure for the processing of generating a corrected harmonic image based on difference value frame data and a predetermined threshold according to the first embodiment.

In general, according to one embodiment, in an ultrasonic diagnostic apparatus includes an ultrasonic probe, a transmission/reception unit, a signal extraction unit, a calculation unit, an area determination unit, a change unit, and an image generation unit.

The ultrasonic probe is configured to a plurality of transducers. The transmission/reception unit supplies driving signals to the transducers, respectively, and generates a reception signal based on an echo signal. The signal extraction unit extracts a harmonic signal and a fundamental wave signal from the reception signal. The calculation unit calculates feature amounts based on values corresponding to amplitudes of the harmonic signal and values corresponding to amplitudes of the fundamental wave signal. The area determination unit determines a predetermined area in a scanned area based on the feature amounts and a predetermined threshold. The change unit changes a value corresponding to an amplitude of the harmonic signal in the predetermined area. The image generation unit generates a corrected harmonic image based on a harmonic signal in the scanned area including the predetermined area having the changed values corresponding to the amplitudes of the harmonic signal.

An ultrasonic diagnostic apparatus according to an embodiment will be described below with reference to the accompanying drawing. The same reference numerals denote constituent elements having almost the same arrangements, and a repetitive description will be made only when required.

First Embodiment

FIG. 1 is a block diagram showing the arrangement of an ultrasonic diagnostic apparatus 1 according to the first embodiment. Referring to FIG. 1, the ultrasonic diagnostic apparatus 1 includes an ultrasonic probe 11, an apparatus main body 12, a display unit 13, and an input unit 14 which is connected to the apparatus main body 12 and serves to input various kinds of instructions, commands, and information from the operator to the apparatus main body 12. In addition, a biometric signal measurement unit (not shown) typified by an electrocardiograph, phonocardiograph, sphygmograph, or respiration sensor and a network may be connected to the ultrasonic diagnostic apparatus 1 via an interface unit 43.

The ultrasonic probe 11 includes piezoelectric transducers as lossless acoustic/electric conversion elements such as piezoelectric ceramic elements. A plurality of piezoelectric transducers are juxtaposed and mounted on the distal end of the ultrasonic probe 11. Assume that in the following description, one piezoelectric transducer forms one channel. Each piezoelectric transducer generates an ultrasonic wave in response to a driving signal supplied from a transmission/reception unit (to be described later). Each piezoelectric transducer generates an echo signal in response to the reception of an ultrasonic wave reflected (to be referred to as a reflected wave hereinafter) by a living tissue of an object.

The apparatus main body 12 includes a transmission/reception unit 21, a B-mode processing unit 23, a storage unit 31, a calculation unit 33, an area determination unit 35, a change unit 37, an image generation unit 39, a control processor (central processing unit to be referred to as a CPU hereinafter) 41, and an interface unit 43. Note that the apparatus main body 12 includes a Doppler processing unit (not shown) which generates a Doppler signal.

The transmission/reception unit 21 includes a trigger generating circuit, a transmission delay circuit, a pulser circuit, a preamplifier circuit, an analog/digital (to be referred to as A/D hereinafter) converter, a reception delay circuit, and an adder (none of which are shown). The pulser circuit repetitively generates rate pulses for the formation of transmission ultrasonic waves at a predetermined rate frequency. A pulse generator repetitively generates rate pulses at a rate frequency of, for example, 5 kHz. These rate pulses are distributed according to a channel count and sent to the transmission delay circuit. The transmission delay circuit gives each rate pulse a delay time necessary to focus an ultrasonic wave into a beam and determine transmission directivity for each channel. The trigger generating circuit applies a voltage pulse to each transducer of the ultrasonic probe 11 at the timing based on this rate pulse, thereby transmitting ultrasonic beams to the object.

The preamplifier circuit amplifies an echo signal received from the object via the ultrasonic probe 11 for each channel. The A/D converter converts each amplified echo signal into a digital signal. The reception delay circuit gives the echo signals converted into digital signals delay times required to determine reception directivity. The adder adds a plurality of echo signals given the delay times. With this addition, the transmission/reception unit 21 generates a reception signal with a reflection component from a direction corresponding to the reception directivity being enhanced. The transmission directivity and the reception directivity determine the comprehensive directivity of ultrasonic transmission/reception (which in turn determines so-called "ultrasonic scanning lines"). Note that the transmission/reception unit 21 may have a parallel reception function of simultaneously receiving echo signals generated on a plurality of scanning lines by one ultrasonic transmission.

The B-mode processing unit 23 includes a signal extraction unit 231, an envelope detector 233, and a logarithmic converter 235. The signal extraction unit 231 extracts a fundamental wave signal and a harmonic signal from a reception signal. A fundamental wave signal is a reception signal having the same frequency as the center frequency (to be referred to as a fundamental frequency hereinafter) of a transmission ultrasonic wave. A harmonic signal is a reception signal having the same frequency as an arbitrary integer multiple of the fundamental frequency. In the following description, for the sake of simplicity, a harmonic signal to be extracted will be referred to as a reception signal having a frequency twice the fundamental frequency (to be referred to as a second-order harmonic signal hereinafter).

More specifically, the signal extraction unit 231 extracts a second-order harmonic signal from a reception signal by cutting a fundamental wave signal and third and higher-order harmonic signals with, for example, a band-limiting filter. The signal extraction unit 231 extracts a fundamental wave signal from a reception signal by cutting harmonic signals with, for example, a band-limiting filter. The signal extraction unit 231 outputs the extracted fundamental wave signal and the second-order harmonic signal to the envelope detector 233.

The envelope detector 233 executes envelope detection of the fundamental wave signal and second-order harmonic signal output from the signal extraction unit 231. The envelope detector 233 outputs the envelope-detected signal to the logarithmic converter 235 (to be described later). Note that the envelope detector 233 may output the envelope-detected signal to the storage unit 31 (to be described later).

The logarithmic converter 235 relatively enhances a weak signal by logarithmically converting the envelope-detected signal. The logarithmic converter 235 outputs the logarithmically converted signal to both the storage unit 31 (to be described later) and the image generation unit 39.

The storage unit 31 stores a plurality of reception delay patterns with different focus depths, control programs for the ultrasonic diagnostic apparatus 1, a diagnostic protocol, various kinds of data such as transmission/reception conditions, logarithmically converted data (to be referred to as fundamental wave data hereinafter) concerning a fundamental wave signal, logarithmically converted data (to be referred to as harmonic data hereinafter) concerning a second-order harmonic signal, the ultrasonic images generated by the image generation unit 39 (to be described later), a calculation program used by the calculation unit 33 (to be described later), a predetermined threshold used by the area determination unit 35 (to be described later), a predetermined value used by the change unit 37 (to be described later), and image processing programs for controlling the calculation unit 33, the area determination unit 35, and the change unit 37. The storage unit 31 stores fundamental wave data for each frame. A set of fundamental wave data in one frame will be referred to as fundamental wave frame data hereinafter. The storage unit 31 stores harmonic data for each frame. A set of harmonic frame data in one frame will be referred to as harmonic frame data hereinafter. Note that the storage unit 31 may store the signals obtained by envelope detection of a fundamental wave signal and a second-order harmonic signal for each frame.

The calculation unit 33 calculates feature amounts throughout a scanned area (frame) based on values corresponding to the amplitudes of harmonic data and values corresponding to the amplitudes of fundamental wave data. A feature amount is an amount concerning an amplitude. For example, a feature amount concerning an amplitude is the difference value (Diff(x, y)) between a value corresponding to an amplitude of harmonic data and a value corresponding to an amplitude of fundamental wave data. In the above sentence, x indicates, for example, a coordinate in the depth direction of a scanning line signal string in ultrasonic scanning, and y indicates a coordinate in the scanning direction. Note that coordinates x and y may be coordinates on the ultrasonic image generated by the image generation unit 39. At this time, values corresponding to the amplitudes of harmonic data are associated with coordinates on the harmonic image generated by the image generation unit 39 based on harmonic data. In addition, values corresponding to the amplitudes of fundamental wave data are associated with coordinates on the fundamental wave image generated by the image generation unit 39 based on fundamental wave data.

A value corresponding to an amplitude is, for example, an amplitude value. Note that it is possible to use a pixel value or a luminance value instead of an amplitude value. For the sake of detailed description, assume also that a scanned area is the heart of an object. Note that the calculation unit 33 may calculate the feature amounts determined by pixel values of the fundamental wave image generated by the image generation unit 39 (to be described later) and pixel values of a harmonic image throughout the entire image.

More specifically, the calculation unit 33 reads out the fundamental wave frame data stored in the storage unit 31. The calculation unit 33 reads out the harmonic frame data stored in the storage unit 31. The calculation unit 33 subtracts an amplitude value (to be referred to as a fundamental amplitude value (Fund(x, y)) hereinafter) of fundamental wave frame data from an amplitude value (to be referred to as a harmonic amplitude value (Harm(x, y)) hereinafter) of harmonic frame data. That is, the calculation unit 33 calculates the difference value Diff(x, y) according to Diff(x, y)=Harm (x, y)−Fund(x, y). Note that the calculation unit 33 may subtract a harmonic amplitude value from a fundamental amplitude value. The calculation unit 33 may also calculate the absolute value of a difference value. With the above differences, the calculation unit 33 generates, for each frame, a set of difference values (to be referred to as difference value frame data hereinafter) at each position on the scanned area which is defined by a coordinate (x) in the depth direction and a coordinate (y) in the scanning direction. When acquiring reception signals throughout a plurality of frames, the apparatus performs the above calculation for each of the plurality of frames.

The area determination unit 35 determines a predetermined area in a scanned area based on the difference value at each position on the scanned area and a predetermined threshold. More specifically, the area determination unit 35 reads out the predetermined threshold stored in the storage unit 31. The area determination unit 35 compares the predetermined threshold with each of the difference values in difference value frame data. The area determination unit 35 specifies a position (x, y) on the scanned area concerning a difference value equal to or more than the predetermined threshold. The operator can change the predetermined threshold via the input unit 14 (to be described later), as needed. The area determination unit 35 determines an area constituted by the specified positions. That is, the predetermined area is an area constituted by specified positions.

A predetermined area concerning a case in which fundamental amplitude values are subtracted from harmonic amplitude values will be described. In general, the amplitude value of a reflected echo (to be referred to as a spontaneous echo hereinafter) from a blood flow in a cardiac cavity is small relative to the amplitude value of a reflected echo (to be referred to as a structure echo hereinafter) from a structure such as the cardiac muscle as a reference. In some case, the difference between an amplitude value of a structure echo and an amplitude value of a spontaneous echo is relatively large in the case of fundamental amplitude values, but is relatively small in the case of harmonic amplitude values. When, therefore, fundamental amplitude values are subtracted from harmonic amplitude values, the value obtained by subtracting the fundamental amplitude value from the harmonic amplitude value of each structure echo differs from that obtained by subtracting the fundamental amplitude value from the harmonic amplitude value of each spontaneous echo. For this reason, a predetermined area constituted by positions on a scanned area at which difference values are equal to or more than a predetermined threshold corresponds to an area where spontaneous echoes exist. When the order of subtraction is reversed, an area where spontaneous echoes exist corresponds to an area where difference values are equal to or less than a predetermined threshold.

The change unit 37 changes values corresponding to the amplitudes of harmonic frame data in a predetermined area determined by the area determination unit 35 to a predetermined value. A value corresponding to an amplitude is, for example, an amplitude value, pixel value, or luminance value. In the following description, a harmonic amplitude value is used as a value corresponding to an amplitude. Calculation using pixel values and luminance values will be described in detail in later modifications. The predetermined value is, for example, 0. Note that the change unit 37 can change harmonic amplitude values in a predetermined area to values corresponding to the magnitudes of difference values. More specifically, the change unit 37 changes the harmonic amplitude values contained in a predetermined area of harmonic frame data to 0. Harmonic frame data obtained by changing the harmonic amplitude values in a predetermined area to 0 will be referred to as harmonic corrected frame data.

Note that the change unit 37 changes values corresponding to the amplitudes of fundamental wave signals in a predetermined area to a predetermined value. The fundamental wave frame data obtained by changing the fundamental amplitude values in a predetermined area to 0 will be referred to as fundamental wave corrected frame data hereinafter. In addition, the change unit 37 may change the tones, brightnesses, luminance values, or pixel values in a predetermined area of the ultrasonic image generated by the image generation unit 39 to a predetermined value.

The image generation unit 39 converts a scanning line signal string in ultrasonic scanning into a scanning line signal string in a general video format typified by a TV format or the like, and generates an ultrasonic diagnostic image as a display image. The image generation unit 39 generates a corrected harmonic image based on harmonic corrected frame data. Note that the image generation unit 39 may generate a harmonic image based on harmonic data. The image generation unit 39 may generate a corrected harmonic image based on harmonic corrected frame data. In addition, the image generation unit 39 may generate a fundamental wave image based on fundamental wave data. The image generation unit 39 may generate a superimposed harmonic image by superimposing a harmonic image on a corrected harmonic image. The image generation unit 39 may also generate a superimposed fundamental wave image by superimposing a fundamental wave image on a corrected fundamental wave image. The image generation unit 39 may also generate a superimposed harmonic wave image by superimposing a fundamental wave image on a corrected fundamental wave image. For example, the image generation unit 39 may generate a superimposed harmonic image by superimposing a harmonic image obtained by assigning blue (Blue) to each pixel on a corrected harmonic image obtained by assigning red (Red) and green (Green) to pixel values outside a predetermined area. At this time, the area of the superimposed harmonic image which is located outside the predetermined area is displayed in white, and the predetermined area is displayed in blue.

Note that the image generation unit 39 may generate a color Doppler image based on the color Doppler signal output from the Doppler processing unit (not shown). The image generation unit 39 can generate a Doppler superimposed image by superimposing a color Doppler image on a predetermined area of a harmonic image or corrected harmonic image.

The CPU 41 reads out the transmission/reception conditions and apparatus control programs stored in the storage unit 31, based on the mode selection, the selection of a reception delay pattern list, and transmission start and end instructions input by the operator with the input unit 14, and controls the apparatus main body 12 in accordance with them. The CPU 41 may control the calculation unit 33, the area determination unit 35, and the change unit 37 in accordance with the image processing programs read out from the storage unit 31.

The interface unit 43 is an interface concerning the input unit 14, a network, an external storage device (not shown), and a biological signal measurement unit (not shown). It is possible to transfer data such as an ultrasonic image, an analysis result, and the like obtained by the apparatus main body 12 to other apparatuses via the interface unit 43 and a network.

The display unit 13 displays ultrasonic images such as a corrected harmonic image, harmonic image, corrected fundamental wave image, fundamental wave image, superimposed harmonic image, and superimposed fundamental wave image based on outputs from the image generation unit 39.

The input unit 14 is connected to the interface unit 43 and inputs various kinds of instruction, commands, information, selections, and settings from the operator to the apparatus main body 12. The input unit 14 includes input devices such as a trackball, switch buttons, mouse, and keyboard (not shown). The input device detects the coordinates of a cursor displayed on the display screen, and outputs the detected coordinates to the CPU 41. Note that the input device may be a touch panel provided to cover the display screen. In this case, the input unit 14 detects a touched and designated coordinates by a coordinate reading principle such as an electromagnetic induction scheme, magnetostriction scheme, or a pressure-sensitive scheme, and outputs the detected coordinates to the CPU 41. When, for example, the operator operates the end button or FREEZE button of the input device 14, the transmission/reception of ultrasonic waves is terminated, and the apparatus main body 12 is set in a pause state. Note that the input unit 14 may input a predetermined threshold to the apparatus main body 12 in accordance with an instruction from the operator. The input unit 14 may also have a dial for adjusting the tones of a predetermined area in accordance with an instruction from the operator.

(Predetermined Area Determination Function)

A predetermined area determination function is a function of determining an area concerning spontaneous echoes in a scanned area based on the harmonic signal and fundamental wave signal extracted from a reception signal. Processing (to be referred to as predetermined area determination processing hereinafter) concerning the predetermined area determination function will be described below.

FIG. 2 is a flowchart showing a procedure for predetermined area determination processing.

Before ultrasonic transmission/reception with respect to an object, the apparatus executes input of patient information, setting and updating of transmission/reception conditions and various kinds of ultrasonic data acquisition conditions, and the like in accordance with instructions from the operator via the input unit 14. The storage unit 31 stores these settings and updates. Upon completion of these input, selection, and setting operations, the operator brings the ultrasonic probe 11 into contact with the body surface of the object at a predetermined position. The transmission/reception unit 21 then supplies driving signals for generating ultrasonic waves to the ultrasonic transducers. With these driving signals, ultrasonic waves are transmitted to the object.

The apparatus generates an echo signal based on the reception of ultrasonic waves (that is, ultrasonic scanning) corresponding to the ultrasonic waves transmitted to the object. The apparatus then generates a reception signal based on the generated echo signal (step Sa1).

Figure 3:
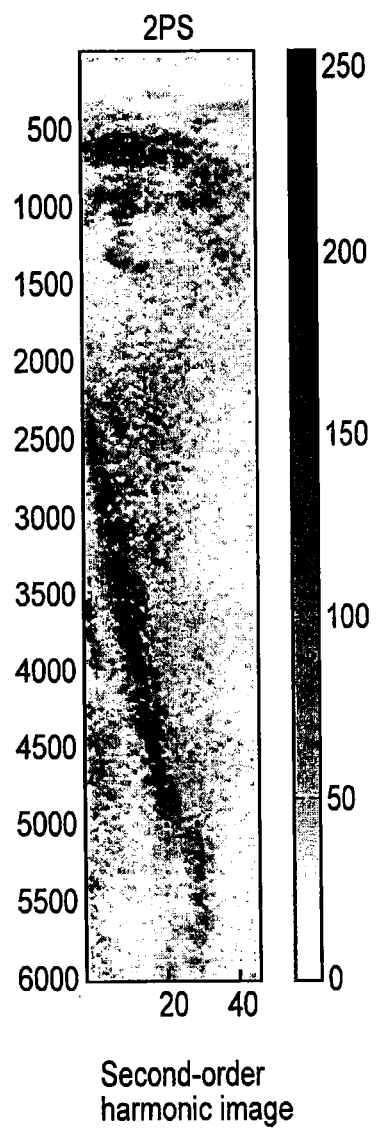
FIG. 3 is a view showing an example of a harmonic image (second-order harmonic image) generated based on harmonic frame data according to the first embodiment.
Figure 4:
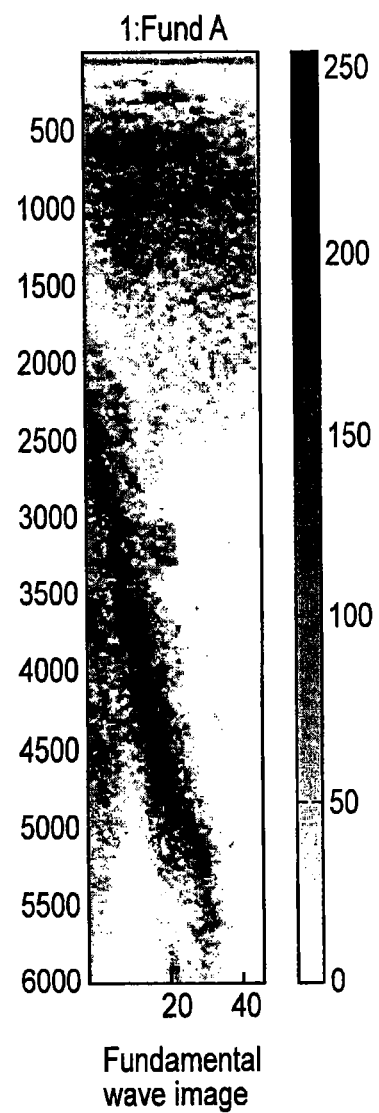
FIG. 4 is a view showing an example of a fundamental wave image (fundamental wave picture) generated based on fundamental wave frame data according to the first embodiment.

The apparatus extracts a harmonic signal and a fundamental wave signal from the reception signal (step Sa2). The apparatus generates harmonic frame data based on the harmonic signal (step Sa3). FIG. 3 is a view showing an example of the harmonic image (second-order harmonic image) generated based on the harmonic frame data. The apparatus generates fundamental wave frame data based on the fundamental wave signal (step Sa4). FIG. 4 is a view showing an example of the fundamental wave image (fundamental wave picture) generated based on the fundamental wave frame data. Note that the gains of the ultrasonic images in FIGS. 3 and 4 are corrected to make the cardiac muscle images have the same luminances. Referring to FIGS. 3 and 4, areas having different luminances are mainly images formed from spontaneous echoes.

Figure 6:
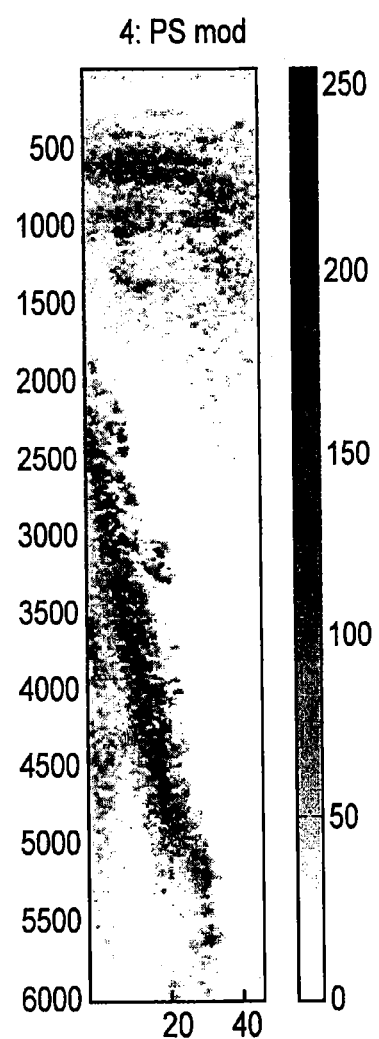
FIG. 6 is a view showing an example of a corrected harmonic image generated based on harmonic corrected frame data according to the first embodiment.

The apparatus generates difference value frame data by subtracting the fundamental wave frame data from the harmonic frame data (step Sa5). FIG. 5 is a view showing an example of the difference value image generated based on the difference value frame data. The difference value image in FIG. 5 is gain-corrected to allow easy visual recognition of an image formed from spontaneous echoes. The apparatus determines a predetermined area in the scanned area based on the difference value frame data and a predetermined threshold (step Sa6). A predetermined threshold is, for example, 0. This predetermined area indicates an area where spontaneous echoes exist. The apparatus generates harmonic corrected frame data by changing the amplitude values of the harmonic frame data in the predetermined area to a predetermined value (step Sa7). The apparatus generates a corrected harmonic image based on the harmonic corrected frame data (step Sa8). FIG. 6 is a view showing an example of the corrected harmonic image generated based on the harmonic corrected frame data. A comparison between FIGS. 3 and 6 clarifies that the image formed from spontaneous echoes is reduced.

(Modification)

This modification differs from the first embodiment in that the apparatus changes, based on a determined predetermined area, the brightness of each pixel value in the predetermined area in a harmonic image to a predetermined brightness. A brightness is, for example, a tone. Note that it is possible to use a luminance value or pixel value instead of the brightness of a pixel value. Constituent elements which operate differently from those in the first embodiment will be described below.

The change unit 37 changes the brightness of each pixel value in a predetermined area in a harmonic image to a predetermined value. The predetermined value is, for example, 0. Note that the change unit 37 may change the brightness of each pixel value in a predetermined area in a fundamental wave image to a predetermined value. The change unit 37 may change each luminance value in a predetermined area in a harmonic image to a predetermined luminance value. A predetermined luminance value is, for example, the minimum or maximum value of luminance. The change unit 37 may also change each luminance value in a predetermined area in a fundamental wave image to a predetermined luminance value. Note that the change unit 37 may change each pixel value in a predetermined area in a displayed harmonic image to a predetermined pixel value. The change unit 37 may change a value corresponding to an amplitude of a harmonic signal in a predetermined area to a predetermined value displayed with a brightness lower than that in a scanned area except for the predetermined area.

The display unit 13 displays a harmonic image obtained by changing the brightness of each pixel value in the predetermined area. The display unit 13 displays a fundamental wave image obtained by changing the brightness of each pixel value in the predetermined area.

With the above arrangement, the following effects can be obtained.

The ultrasonic diagnostic apparatus 1 can determine an area where spontaneous echoes exist by using a harmonic signal and a fundamental wave signal. Changing each amplitude value or brightness in the determined area can generate an ultrasonic image with a reduced influence of spontaneous echoes. According to the ultrasonic diagnostic apparatus 1, this improves the visibility of, for example, the movement of a cardiac valve or the visibility of a structure such as the inner membrane of the heart in a B-mode image such as a harmonic image. In addition, it is possible to generate a Doppler superimposed image by superimposing a color Doppler image on a predetermined area of a harmonic image or corrected fundamental wave image. This makes it possible to superimpose a color Doppler image on a region which ought to be a blood flow region. This in turn makes it possible to display the color Doppler image on the region which ought to be the blood flow region.

In addition, when the technical idea of the ultrasonic diagnostic apparatus 1 is to be implemented by a medical image processing apparatus as a modification of the above embodiment, for example, the apparatus includes the constituent elements in the dotted line in the block diagram of FIG. 1. At this time, the processing in predetermined area determination in the modification is the same as that in the first embodiment except that the processing in step Sa1 is changed to the processing of reading out a received signal from the storage unit 31. In addition, each function according to each embodiment can be implemented by installing programs for executing the processing in a computer such as a workstation and expanding them in the memory. In this case, the programs which can cause the computer to execute the corresponding techniques can be distributed by being stored in recording media such as magnetic disks (Floppy® disks, hard disks, and the like), optical disks (CD-ROMs, DVDs, and the like), and semiconductor memories.

Second Embodiment

The second embodiment will be described below with reference to the accompanying drawings.

FIG. 7 is a block diagram showing an example of the arrangement of an ultrasonic diagnostic apparatus 1 according to the second embodiment.

The second embodiment differs from the first embodiment in terms of constituent elements in that it includes a filter unit 25. Constituent elements in the second embodiment which operate differently from those in the first embodiment will be described below.

The filter unit 25 generates the first frame data obtained by applying a spatial filter to the harmonic frame data stored in a storage unit 31. The filter unit 25 generates the second frame data by applying a spatial filter to the fundamental wave frame data stored in the storage unit 31. The spatial filter is, for example, a low pass filter (to be referred to as an LPF hereinafter). The LPF spatially smoothes fundamental wave frame data and harmonic frame data. For example, the LPF suppresses speckle noise associated with the cardiac muscle.

A calculation unit 33 calculates an average value (to be referred to as the first average value hereinafter) by using a plurality of amplitude values (HarmA(x, y)) contained in the first frame data. The calculation unit 33 calculates the first average value by dividing the sum ($\Sigma x, y$(HarmA(x, y))) of a plurality of amplitude values of the first frame data by the number of samples of the first frame data. The calculation unit 33 calculates an average value (to be referred to as the second average value hereinafter) by using a plurality of amplitude values (FundA(x, y)) contained in the second frame data. The calculation unit 33 calculates the second average value by dividing the sum ($\Sigma x, y$(FundA(x, y))) of a plurality of amplitude values of the second frame data by the number of samples of the second frame data.

The calculation unit 33 standardizes each of the plurality of amplitude values (HarmA(x, y)) contained in the first frame data with the first average value. The first frame data standardized with the first average value will be referred to as the first standardized frame data hereinafter. The calculation unit 33 standardizes each of the plurality of amplitude values contained in the second frame data with the second average value. The second frame data standardized with the second average value will be referred to as the second standardized frame data hereinafter.

This standardization will make the average value of the amplitudes (HarmN(x, y)) in the first standardized frame data become almost equal to that of the amplitudes (FundN(x, y)) in the second standardized frame data. At this time, for example, each amplitude value (HarmN(x, y)) in the first standardized frame data about a structure such as the cardiac muscle is almost equal to a corresponding amplitude value (FundN(x, y)) in the second standardized frame data at the same position in the scanned area. For example, when an image generated based on the first standardized frame data is compared with an image generated based on the second standardized frame data, the structure is displayed with the same luminance in both the images. That is, the luminances of the structure in the second-order harmonic image in FIG. 3 are almost the same as those of the structure in the fundamental wave image in FIG. 4 at the same positions in the scanned area.

The calculation unit 33 calculates feature amounts determined by the amplitude values (HarmN(x, y)) in the first standardized frame data and the amplitude values (FundN(x, y)) in the second standardized frame data. A feature amount is the first difference value (Diff(x, y)) obtained by subtracting each amplitude value (FundN(x, y)) in the second standardized frame data from a corresponding amplitude value (HarmN(x, y)) in the first standardized frame data. The calculation unit 33 generates a set of first difference values (to be referred to as the third frame data hereinafter) at the respective positions defined by coordinates (x) in the depth direction and coordinates (y) in the scanning direction for each frame. The calculation unit 33 calculates the differences between the amplitude values in the first and second standardized frame data, and hence the amplitude values concerning a structure such as the cardiac muscle become almost 0. Amplitude values which are not 0 in the third frame data are those originating from spontaneous echoes.

An area determination unit 35 determines a predetermined area in a scanned area based on the first difference values (Diff(x, y)) in the third frame data and a predetermined threshold. More specifically, the area determination unit 35 reads out the predetermined threshold stored in the storage unit 31. The area determination unit 35 compares each first difference value in the third frame data with the predetermined threshold. The area determination unit 35 specifies a position (x, y) on a scanned area concerning the first difference value equal to or more than the predetermined threshold. The area determination unit 35 determines the area constituted by the specified positions. That is, the predetermined area is the area constituted by the specified positions.

In the second embodiment, it is possible to set the predetermined threshold to 0. For standardization, amplitude values originating from structure echoes in the first standardized frame data are almost the same as those in the second standardized frame data. On the other hand, the amplitude values in the first standardized frame data originating from spontaneous echoes are larger than those in the second standardized frame data. A predetermined area constituted by positions on a scanned area where the first difference values are positive corresponds to an area where spontaneous echoes exist. When the order of subtraction is reversed, an area where spontaneous echoes exist corresponds to an area where the first difference values are negative. FIG. 8 is a view showing an example of a correspondence table between structure and spontaneous echoes and the signs of difference values in association with the order of subtraction.

A change unit 37 changes values corresponding to the amplitudes of harmonic frame data in a predetermined area to a predetermined value. A value corresponding to an amplitude is, for example, an amplitude value. For example, a value corresponding to an amplitude may be a pixel value or a luminance value. In the following description, an amplitude value (to be referred to as a harmonic amplitude value (to be referred to as (Harm(x, y)) hereinafter) is used as a value corresponding to an amplitude. The predetermined value is, for example, the second difference value obtained by subtracting the first difference value in the third frame data from a harmonic amplitude value in the predetermined area. Note that the calculation unit 33 may calculate the second difference value. The harmonic frame data obtained by changing each harmonic amplitude value in a predetermined area to the second difference value will be referred to as harmonic corrected frame data hereinafter.

An image generation unit 39 generates a corrected harmonic image based on harmonic corrected frame data. Note that the image generation unit 39 can generate a harmonic image by changing each tone in a predetermined area to a predetermined value based on harmonic frame data and the predetermined area. Note that the image generation unit 39 may also generate a color Doppler image based on the color Doppler signal output from a Doppler processing unit (not shown). The image generation unit 39 can also generate a Doppler superimposed image by superimposing a color Doppler image on a predetermined area in a harmonic image or corrected harmonic image.

(Predetermined Area Determination Function)

A predetermined area determination function is a function of determining an area concerning spontaneous echoes in a scanned area based on the harmonic signal and fundamental wave signal extracted from a reception signal. Processing (to be referred to as predetermined area determination processing hereinafter) concerning the predetermined area determination function will be described below.

Figure 9:
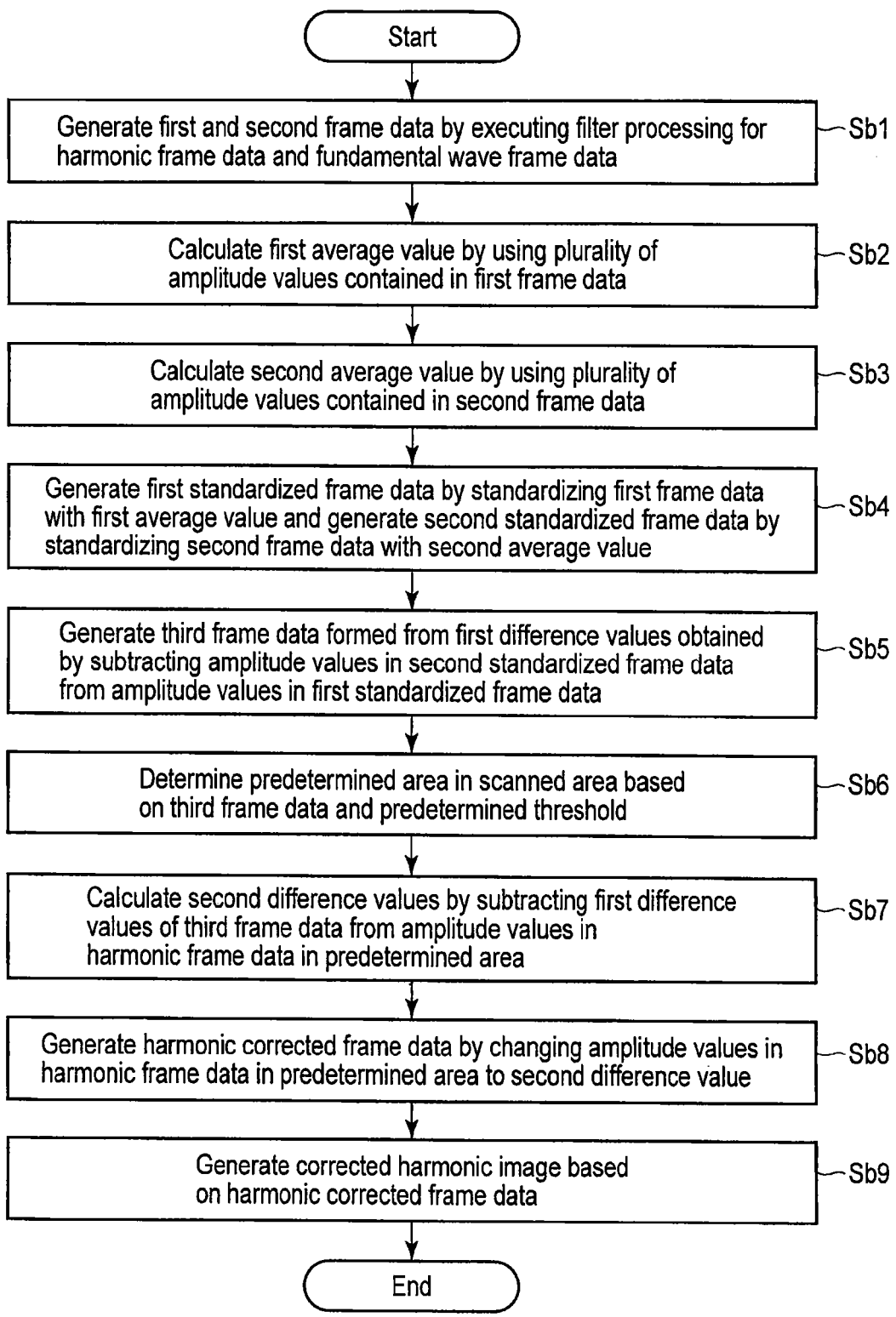
FIG. 9 is a flowchart showing a procedure for the processing of generating a corrected harmonic image based on difference value frame data and a predetermined threshold according to the second embodiment.

FIG. 9 is a flowchart showing a procedure for predetermined area determination processing.

The apparatus extracts a harmonic signal and a fundamental wave signal from the reception signal generated by a transmission/reception unit 21. The apparatus generates harmonic frame data based on a harmonic signal. The apparatus generates fundamental wave frame data based on a fundamental wave signal. The apparatus generates the first and second frame data by executing filter processing for the harmonic frame data and the fundamental wave frame data (step Sb1).

The apparatus calculates the first average value by using a plurality of amplitude values in the first frame data (step Sb2). The apparatus calculates the second average value by using a plurality of amplitude values in the second frame data (step Sb3). The apparatus generates the first standardized frame data by standardizing the first frame data with the first average value, and generates the second standardized frame data by standardizing the second frame data with the second average value (step Sb4). The apparatus generates the third frame data constituted by the first difference values obtained by subtracting the amplitude values in the second standardized frame data from those in the first standardized frame data (step Sb5).

The apparatus determines a predetermined area in the scanned area based on each first difference value and the predetermined threshold in the third frame data (step Sb6).

The apparatus calculates the second difference values by subtracting the first difference values in the third frame data from the amplitude values in the harmonic frame data (step Sb7). The apparatus generates harmonic corrected frame data by changing each amplitude value in the harmonic frame data in the predetermined area to the second difference value (step Sb8). The apparatus generates a corrected harmonic image based on the harmonic corrected frame data (step Sb9).

According to the above arrangement, the following effects can be obtained.

The ultrasonic diagnostic apparatus 1 applies a filter to a harmonic signal and a fundamental wave signal to remove noise such as speckle noise. The apparatus standardizes the harmonic signal and the fundamental wave signal, for which filtering has been executed, with the average values of the amplitudes to reduce amplitude differences between the harmonic signal and the fundamental wave signal in association with a structure. The apparatus can derive an increase in amplitude value due to spontaneous echoes by using the standardized harmonic signal and standardized fundamental wave signal. This makes it possible to determine an area where spontaneous echoes exist. In addition, it is possible to generate an ultrasonic image with a reduced influence of spontaneous echoes by subtracting increases in amplitude value due to spontaneous echoes from a harmonic signal in the determined area. According to the ultrasonic diagnostic apparatus 1, this improves the visibility of, for example, the movement of a cardiac valve or the visibility of a structure such as the inner membrane of the heart in a B-mode image such as a harmonic image. In addition, it is possible to generate a Doppler superimposed image by superimposing a color Doppler image on a predetermined area of a harmonic image or a corrected harmonic image. This makes it possible to superimpose a color Doppler image on a region which ought to be a blood flow region. This in turn makes it possible to display the color Doppler image on the region which ought to be the blood flow region.

In addition, when the technical idea of the ultrasonic diagnostic apparatus 1 is to be implemented by a medical image processing apparatus as a modification of the above embodiment, for example, the apparatus includes the constituent elements in the dotted line in the block diagram of FIG. 7. At this time, the processing in predetermined area determination in the modification is the same as that in the second embodiment except that the processing in step Sb1 is changed to the processing of reading out the first and second frame data from the storage unit 31. In addition, each function according to each embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

Some embodiments of the present invention have been described above. However, these embodiments are presented merely as examples and are not intended to restrict the scope of the invention. These novel embodiments can be carried out in various other forms, and various omissions, replacements, and alterations can be made without departing from the gist of the invention. The embodiments and their modifications are also incorporated in the scope and the gist of the invention as well as in the invention described in the claims and their equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe including a plurality of transducers;
a transmission/reception unit, implemented by circuitry, configured to supply driving signals to each of the transducers and generate reception signals based on echo signals;
a signal extraction unit, implemented by the circuitry, configured to extract a harmonic signal and a fundamental wave signal from each reception signal;
a calculation unit, implemented by the circuitry, configured to calculate a feature amount concerning a scanned area based on values corresponding to amplitudes of the harmonic signals and values corresponding to amplitudes of the fundamental wave signals;
an area determination unit, implemented by the circuitry, configured to determine an area in the scanned area based on the feature amount and a predetermined threshold;
a change unit, implemented by the circuitry, configured to change the values corresponding to the amplitudes of the harmonic signals in the determined area; and
an image generation unit, implemented by the circuitry, configured to generate a corrected harmonic image based on the harmonic signals in the scanned area including the determined area having the changed values corresponding to the amplitudes of the harmonic signals.

2. The apparatus of claim 1, wherein the feature amount comprises a difference between the values corresponding to the amplitudes of the harmonic signals and the values corresponding to the amplitudes of the fundamental wave signals at a plurality of points in the scanned area.

3. The apparatus of claim 1, wherein the change unit is configured to change the values corresponding to the amplitudes of the harmonic signals in the determined area to predetermined values.

4. The apparatus of claim 1, wherein the values corresponding to the amplitudes of the harmonic signals and the values corresponding to the amplitudes of the fundamental wave signals are associated with coordinate information of an ultrasonic image generated by the image generation unit.

5. The apparatus of claim 1, wherein the change unit is configured to change the values corresponding to the amplitudes of the harmonic signals in the determined area to predetermined values for display with brightness lower than brightness of the scanned area excluding the determined area.

6. The apparatus of claim wherein the change unit is configured to change the values corresponding to amplitudes of the fundamental wave signals in the determined area to predetermined values, and
the image generation unit is configured to generate a corrected fundamental wave image corresponding to the scanned area based on the changed fundamental wave signals and the fundamental wave signals in the scanned area excluding the determined area.

7. The apparatus of claim 6, wherein the image generation unit is configured to:
generate a fundamental wave image based on the fundamental wave signals;
generate a harmonic image based on the harmonic signals; and
generate a superimposed image by superimposing at least one of the corrected harmonic image and the corrected fundamental wave image on at least one of the fundamental wave image and the harmonic image.

8. The apparatus of claim 1, further comprising a filter unit, implemented by the circuitry, configured to execute spatial filter processing for the harmonic signals and the fundamental wave signals,
wherein the calculation unit is configured to calculate, throughout the scanned area, a difference between the values corresponding to the amplitudes of the spatial-filtered harmonic signals and the values corresponding to the amplitudes of the spatial-filtered fundamental wave signals.

9. The apparatus of claim wherein the calculation unit is configured to:
standardize the values corresponding to the amplitudes of the harmonic signals based on an average of the amplitude of the harmonic signals throughout the scanned area;
standardize the values corresponding to the amplitudes of the fundamental wave signals based on an average of the amplitudes of the fundamental wave signals throughout the scanned area; and
calculate, throughout the scanned area, a difference between the standardized values corresponding to the amplitudes of the harmonic signals and the standardized values corresponding to the amplitudes of the fundamental wave signals.

10. The apparatus of claim 1, further comprising an input device configured to input the predetermined threshold.

11. A medical image processing apparatus comprising:
a storage configured to store reception signals generated by an ultrasonic diagnostic apparatus; and
circuitry configured to
extract a harmonic signal and a fundamental wave signal from each reception signal,
calculate a feature amount concerning a scanned area based on values corresponding to amplitudes of the harmonic signals and values corresponding to amplitudes of the fundamental wave signals,
determine an area in the scanned area based on the feature amount and a predetermined threshold,
change the values corresponding to the amplitudes of the harmonic signals in the determined area, and
generate a corrected harmonic image based on the harmonic signals in the scanned area including the determined area having the changed values corresponding to the amplitudes of the harmonic signals.

12. The apparatus of claim 11, wherein the feature amount comprises differences between the values corresponding to the amplitudes of the harmonic signals and the values corresponding to the amplitudes of the fundamental wave signals.

* * * * *